United States Patent [19]

Drews

[11] 3,970,250
[45] July 20, 1976

[54] ULTRASONIC LIQUID ATOMIZER

[75] Inventor: Wolf-Dietrich Drews, Munich, Germany

[73] Assignee: Siemens Aktiengesellschaft, Berlin & Munich, Germany

[22] Filed: Sept. 24, 1975

[21] Appl. No.: 616,147

[30] Foreign Application Priority Data
Sept. 25, 1974 Germany............................ 2445791

[52] U.S. Cl. .............................. 239/102; 239/338; 239/351; 239/370
[51] Int. Cl.² ......................... B05B 3/14; B05B 7/28
[58] Field of Search ............... 239/4, 101, 102, 338, 239/351, 369–371; 259/DIG. 44

[56] References Cited
UNITED STATES PATENTS

| | | |
|---|---|---|
| 3,224,677 | 12/1965 | Schmidt et al. ...................... 239/101 |
| 3,738,574 | 6/1973 | Guntersdorfer et al. ........... 239/102 |
| 3,901,443 | 8/1975 | Mitsui et al. ........................ 239/102 |
| 3,904,896 | 9/1975 | Guntersdorfer ...................... 310/8.1 |
| 3,918,640 | 11/1975 | Piccino et al. .................. 239/338 X |

Primary Examiner—Robert S. Ward, Jr.
Attorney, Agent, or Firm—Hill, Gross, Simpson, Van Santen, Steadman, Chiara & Simpson

[57] ABSTRACT

An ultrasonic liquid atomizer of the type having an piezoelectric vibrating system with the vibrations from an piezoelectric transducer being transmitted to an atomizer plate through conical members wherein the atomizer plate is positioned interiorly of a chamber defining member adjacent a discharged orifice and blower means are positioned to induce an air flow through the chamber defining member past the atomizer plate to the orifice providing a jet-like flow past the atomizer plate periphery.

11 Claims, 2 Drawing Figures

ULTRASONIC LIQUID ATOMIZER

BACKGROUND OF THE INVENTION

1. Field of the Invention

This invention relates to atomizers and more particularly to ultrasonic liquid atomizers.

2. Prior Art

U.S. Pat. application Ser. No. 269,935 now U.S. Pat. No. 3,904,896 to Guntersdorfer, shows a piezoelectric vibrating system for atomizing liquids. In accordance with the teachings of that patent, and particularly in accordance with FIG. 2 thereof, the vibrations produced by a piezo-ceramic transducer are transmitted to a liquid atomizing atomizer plate by means of a conical transformer member, see also U.S. Pat. No. 3,738,574 to Guntersdorfer et. al.

This prior known type of piezo-ceramic electric vibrating system can be protected against moisture or other fluid damage which can occur when an atomizing conductive liquids by supporting the conical transformer in the neighborhood of a vibrational mode line through an attached mounting ring. The mounting ring can then constitute the end of a housing defining member which encloses the piezoelectric vibratory system. In this manner, a portion of the conical transformer will be positioned interior of the housing defining member. The housing defining member can also contain the electric excitation system for the transducer as well as the transducer.

It is also known from German laid open patent application P23 08 584, the teachings of which are herein incorporated by reference, that liquid can be supplied to the atomizer plate by means of a bore provided through the conical transformer along the axis of rotation which intersects with the another bore positioned at the level of the mounting ring and extending perpendicular to the axis of rotation of the conical transformer.

During continuous operation of such above described piezoelectric vibratory systems, liquid filaments or films can develop at the edge of the atomizer plate. When this occurs, it is possible per the underside of the atomizer plate to also become partially coated with liquid. During atomizing, droplets of such liquid from the underside of the atomizer can then be accelerated onto the conical transformer. This has the disadvantage in that such contact with the conical transformer can alter the residence frequency of the vibratory system in such a manner that performance of the atomizer may be reduced. It would therefore be an advance in the art to provide a piezoelectric vibratory system of the type above described in which means are provided to prevent the formation of liquid films at the edge of the atomizer plate and to prevent the formation of liquid accumulations on the undersurface of the atomizer plate.

SUMMARY OF THE INVENTION

This invention overcomes the above described difficulties of the prior art and positions the atomizer plate interior of an outer housing defining member adjacent a discharge orifice thereof. Preferably, the outer housing defining member reduces in cross section adjacent the orifice and the atomizer plate is positioned interiorly of the outer housing defining member somewhat in the manner of an internally positioned stopper which is in spaced relation to the orifice. In this manner, an annular area is defined between the periphery of the atomizer plate and the inner periphery of the orifice. Blower means are provided to induce an air flow through the outer housing defining member, around the atomizer plate periphery, and through the orifice. This air flow produces an accelerated jet air flow past the rim of the atomizer plate, due to the positioning of the orifice and the atomizer plate.

Due to the air flow past the rim of the atomizer plate, no liquid filming or liquid filament build-up can occur of a type which will result in liquid being transferred to the underside of the plate.

Additionally, in the preferred embodiment illustrated, the spacing between the atomizer plate and the discharge orifice is regulatable so as to control air flow past the atomizer plate and out of the orifice.

Additionally, in the preferred embodiment illustrated, the atomizer plate and the housing which encloses the piezoelectric vibratory system can be mounted interiorly of the outer housing defining member in a manner which aids in directing the air flow. A fan positioned interiorly of the outer housing defining member can draw air from intake orifices located below the vibratory system to provide the air flow.

It is therefore an object of this invention to provide an improved ultrasonic liquid atomizer.

It is another more particular object of this invention to provide piezoelectric vibratory system liquid atomizer, wherein the atomizer plate of the vibratory system is positioned interior of a chamber defining member in relative close spaced relation to an orifice thereof, the chamber being dimensioned to provide a jet-like air flow around the rim of an atomizer plate and through the orifice, and having means inducing the air flow.

It is another more particular object of this invention to provide a piezoelectric vibratory liquid atomizer having an atomizing plate positioned interiorly of an aerodynamicly dimensioned chamber defining member, the plate being positioned adjacent an outlet orifice, and means being provided to change the spacing between the vibratory plate and the orifice.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

DESCRIPTION OF THE PREFERRED EMBODIMENTS

Figure 1:
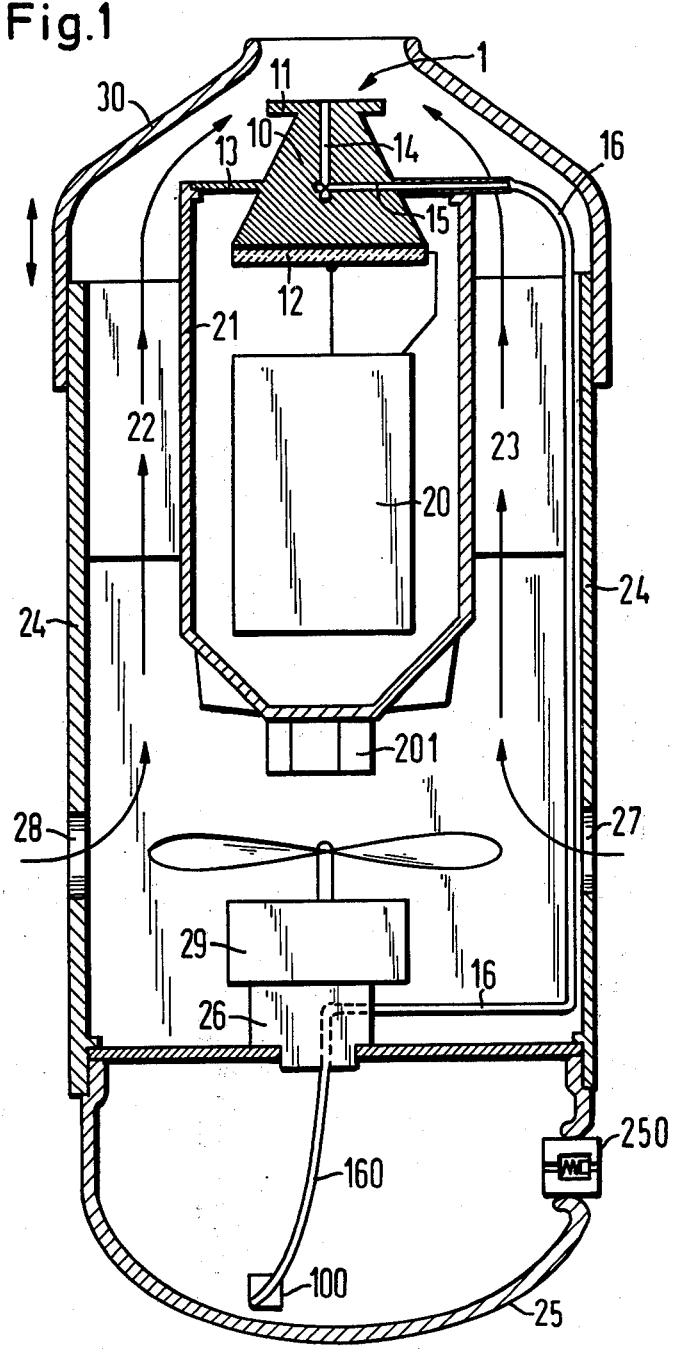
FIG. 1 is a diagrammatic cross sectional view of a liquid atomizer according to this invention.

FIG. 1 illustrates, in cross section, an atomizer according to this invention. The vibratory system 1 includes an atomizer plate 11, a conical transformer member 10, and a piezoelectric transducer 12. The transducer is constructed of one or more piezo-ceramic laminae which have metalized areas for connection to an electronic excitation system 20. In the neighborhood of a vibrational node line, the conical transformer 10 is equipped with a mounting ring 11 extending outwardly therefrom, the vibratory system 1 is attached to a liquid tight inner housing member 21 by means of the mounting ring 13, which, in the embodiment illustrated may form an end wall for the inner housing 21. The housing 21 has the electronic excitation system 20 positioned therein. A liquid transmitting conduit 16 supplies liquid to the atomizer plate 11 through bores 14, 15 extending through the conical transformer section. A reservoir 25 is positioned, in the embodiment illustrated, at a bottom end of an outer housing member 24. The conduit 16 is in communication with the reservoir 25 through a pump 26 which provides a forced supply of liquid from the reservoir to the atomizer plate 11 through the conduits 16.

The atomizer system 1, and the inner housing 21 are mounted interiorly of the outer housing member 24 by means of mounting plates 22 and 23 which function to centrally position the atomizer plate within the outer housing and with respect to a discharge orifice of the outer housing 24.

The outer housing includes air suction openings 27 and 28 which provide air inlets. An internally mounted fan member 29 positioned below the inner housing 21 provides for air flow in the direction of the arrows past the atomizer plate to the discharge orifice. Possible swirling and eddy formations in the air flow are prevented by the mounting plates 22 and 23 which may be dimensioned and configured to maintain a laminar, or, in the embodiment illustrated, substantially axial air flow.

On the side of the inner housing 21 opposite the atomizer plate 11, components of the electronic excitation system, particularly those components which require cooling, can be attached. For example, a transistor with cooling vanes 201, can be attached to that side of the inner housing 21. Therefore, because of the air flow from the fan past the component 201, it will advantageously be cooled.

In the preferred embodiment, the atomizer plate 11 is located adjacent a housing configuration which will provide a jet flow. The configuration, 30, is dimensioned to tapper the internal diameter of the outer housing 24 to the point of the discharge orifice. In this manner, an increase in flow velocity of the air will occur. Between the rim or inner periphery of the outlet and the outer periphery of the atomizer plate 11, an annular space will be defined. Because the space has a relatively small cross-sectional area, the air flow therepast will have relatively high velocity. This increase in velocity assures that no liquid films or filaments will develop at the peripheral edges of the atomizer plate 11 and particularly, no films or filaments of the type which could result in transfer of liquid to the underside of the atomizer plate. Additionally, it is assured that no evaporation deposits will be formed either on the atomizer plate or on the adjacent walls of the housing 24.

Figure 2:
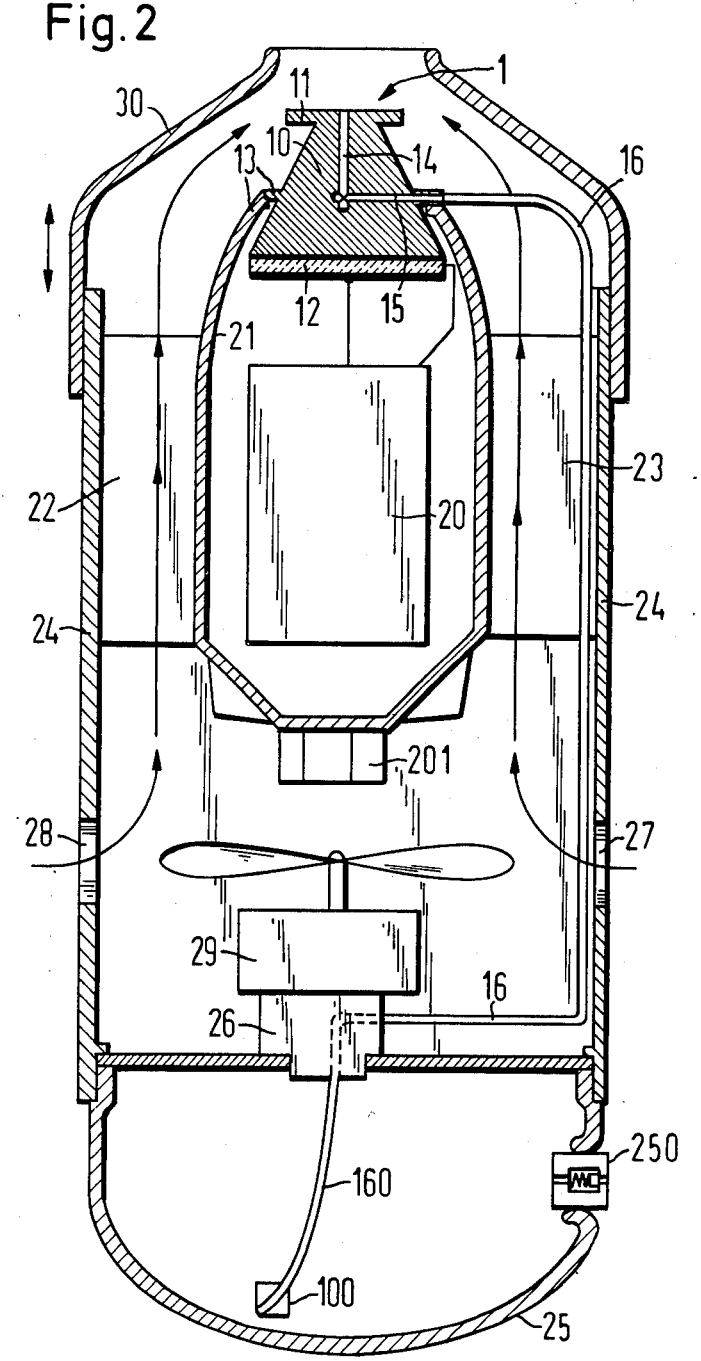
FIG. 2 is a view similar to FIG. 1 illustrating a modified form of the liquid atomizer of this invention.

As an additional feature, in the preferred embodiment, the gap between the inner periphery of the housing at the outlet orifice and the outer periphery of the atomizer plate is made adjustable. This is illustrated in FIGS. 1 and 2 by the provision of a cap member for the housing 24 which is axially movable in the direction indicated by the arrow exterior of the housing. In this manner, the cross sectional area of the gap between the discharge orifice and the atomizer plate can be varied so that the discharge angle of the air stream leaving the jet area or, if a liquid is being atomized, the discharge angle of the aerosol spray, can be varied. Advantageously, relatively small angles on the order of about 5° can be obtained.

It will be apparent from a review of FIGS. 1 and 2 that the inner housing 21 is preferably positioned with respect to the outer housing 24 that an inner and outer defined double walled space is created for passage of the air jet. In order to improve the air flow, the inner housing 21 enclosing the electrical excitation system may be dimensioned as an aerodynamic body around which the air flow generated by the fan 29 can optimumly flow. FIG. 2 illustrates a specific example of the formation of the inner housing 21 as an aerodynamic body wherein the housing 21 slopes to the point of joinder with a mounting ring 13 in a manner which provides an approximate continuous transition between the outer periphery of the inner housing 21 and the conical transformer 10.

In the specific embodiments, the atomizer of FIGS. 1 or 2 can be designed for battery operation or for connection to exterial energy supply sources such as, for example, a typical a.c. power outlet. In the figures, in order to simplify the views, no battery holder or electric cord has been shown, however, they can be provided in a manner obvious to those skilled in the art. For example, a battery holder could be attached beneath the liquid reservoir 25.

Further, it is advantageous if the atomizer can be constructed to operate in any angular position. To insure that the pump 26 will deliver liquid to the atomizer plate 11, a flexible liquid pick-up conduit 160 can be provided extending into the reservoir 25. Provision of a weight 100 at the inlet end of the conduit 160 will insure constant flow through the conduits.

In order to provide pressure compensation in the reservoir 25, the orifice thereto can be provided with a compensating valve closing member 250.

The atomizer of this invention is usable in numerous fields and embodiments and can, for example, be used for atomizing cosmetics or for the production of medicinal aerosols.

It can therefore be seen from the above that this invention provides a liquid atomizer utilizing a piezoelectric vibratory system with the vibrations of a piezoelectric transducer transmitted to an atomizer plate through a conical transformer, the transformer having a mounting ring located at a vibratory node which mounting ring is used to attach the vibratory system in a liquid tight manner to an inner housing containing the transducer and other components of the electronic excitation system. The inner housing is positioned in an outer housing with the atomizer plate closely spaced to a discharge orifice in a manner defining an annular gap between the discharge orifice of the outer housing and the periphery of the atomizer plate. A blower means in association with the housing provides a continuous air flow past the periphery of the atomizer plate in the area of the gap to insure that liquid films and filaments do not accumulate adjacent the periphery of the atomizer plate. In a preferred embodiment, the gap is adjustable to control discharge angles.

Although the teachings of my invention have herein been discussed with reference to specific theories and embodiments, it is to be understood that these are by way of illustration only and that others may wish to utilize my invention in different designs or applications.

I claim as my invention

1. An ultrasonic liquid atomizer utilizing a piezoelectric vibratory system with the vibrations of an piezoelectric transducer transmitted to a liquid atomizer plate by a conical transformer comprising: a housing defining an air flow chamber having an outlet therefrom, an atomizer plate positioned in said housing means adjacent the outlet defining an air flow jet area around the atomizer plate and through the outlet and blower means inducing an air flow through the housing past the atomizer plate and thence through the outlet.

2. The atomizer of claim 1 wherein the atomizer plate is positioned with respect to the discharge outlet to define an annular air flow area between a periphery of the atomizer plate and the inner periphery of the housing at the discharge outlet.

3. An atomizer according to claim 2 wherein the transformer has a fluid supply bore extending at least partially along an axis of rotation of the transformer and terminating at an exterior surface of the atomizer plate, and means defining a liquid flow path to said bore for supply of liquid to be atomized to the atomizer plate.

4. An atomizer according to claim 1 wherein the transformer has a vibrational node area positioned intermediate the transducer and the atomizer plate, a mounting ring attached to said transformer adjacent said vibrational node area, the mounting ring attached to an inner housing member in a manner forming an end cap for said inner housing member with a portion of the transformer and said transducer interior of said inner housing member, said inner housing member supported interior of said chamber defining member by means of support members, said support members lying in a path of air flow through the chamber defining member, the chamber defining member having an internal configuration effective to direct air past said inner housing member around the inner housing member axially of the inner housing member towards the atomizer plate and the discharge orifice.

5. An atomizer according to claim 4 wherein the said support means direct the air flow towards the discharge orifice.

6. The atomizer of claim 2 wherein means are provided to adjust the size of the annular air flow gap between the periphery of the atomizer plate and the inner periphery of the housing at the discharge orifice.

7. A liquid atomizer comprising: an outer housing, and an inner housing, a piezoelectric vibratory system including a piezoelectric transducer attached to an atomizer plate through an intermediately positioned conical transformer, the transformer having a mounting ring intermediate the transducer and the atomizer plate, the mounting ring positioned approximately at a vibratory node area of the conical transformer, the mounting ring forming an end cap for the inner housing, the inner housing mounted in the outer housing through support means extending between the inner and outer housing with the atomizer plate positioned adjacent a discharge orifice of the outer housing, a peripheral gap between a periphery of the atomizer plate and an inner periphery of the discharge orifice, blower means interior of said outer housing providing an air flow through said outer housing past said atomizer plate periphery and through said discharge orifice, and liquid conduit means providing a flow of liquid to be atomized to an exterior surface of the atomizer plate.

8. The atomizer of claim 7 wherein the conduit means includes a bore extending for at least a portion of its length along a rotational axis of the transformer and open to the outside surface of the atomizer plate remote from the transducer, another portion of said bore intersecting with the said portion at substantially right angles, the said another portion extending to the exterior of the said transformer at approximately the level of the mounting ring and second conduit means communicating the said another portion to a liquid source.

9. A liquid atomizer comprising: an outer housing having interior walls, portions of which converge to a discharge orifice from said housing, a piezoelectric vibratory system within said housing, said piezoelectric vibratory system including a transducer attached to an atomizer plate through an intermediately positioned transformer, the atomizer plate positioned adjacent the discharge orifice interiorly of the housing and having peripheral portions of the atomizer plate spaced from the periphery of the discharge orifice defining an air flow space between the periphery of the atomizer plate and the periphery of the orifice, and blower means associated with the housing inducing an air flow past the periphery of the atomizer plate, through the air flow space and out of said discharge orifice.

10. The atomizer of claim 9 wherein means, including the configuration of the interior wall surfaces of the housing and the positioning of the piezoelectric vibratory system within the housing, are provided to insure a relatively high velocity air flow past the said periphery of the atomizer plate through the said air flow space and out the said orifice.

11. An atomizer according to claim 10 wherein means are provided for varying the air flow space by movement of the discharge orifice with respect to the atomizer plate.

* * * * *